United States Patent [19]

Rosen et al.

[11] Patent Number: 5,972,625
[45] Date of Patent: *Oct. 26, 1999

[54] ASSAYS FOR INHIBITORS OF LEUKOCYTE ADHESION

[75] Inventors: Steven D. Rosen, San Francisco; Mark Singer, Berkeley, both of Calif.; Yasuyuki Imai, Tokyo, Japan

[73] Assignee: The Regents of the University of California, Oakland, Calif.

[*] Notice: This patent is subject to a terminal disclaimer.

[21] Appl. No.: 08/886,095

[22] Filed: Jul. 2, 1997

Related U.S. Application Data

[63] Continuation of application No. 08/425,362, Apr. 18, 1995, abandoned, which is a continuation-in-part of application No. 08/132,582, Oct. 6, 1993, abandoned, which is a division of application No. 07/695,805, May 6, 1991, Pat. No. 5,318,890.

[51] Int. Cl.$^6$ .................................................. G01N 33/53
[52] U.S. Cl. ......................... 435/7.2; 435/7.1; 435/7.24; 435/7.71; 435/7.72; 435/7.8; 435/7.9; 435/7.91; 435/7.92; 435/7.93; 435/7.94; 435/7.95
[58] Field of Search ........................ 435/7.1, 7.2, 7.24, 435/7.72, 7.91, 7.94; 530/387.1, 395

[56] References Cited

U.S. PATENT DOCUMENTS

| | | |
|---|---|---|
| 3,654,090 | 4/1972 | Schuurs et al. . |
| 4,134,792 | 1/1979 | Boguslaski et al. . |
| 5,211,937 | 5/1993 | Brandley et al. . |
| 5,318,890 | 6/1994 | Rosen et al. . |

OTHER PUBLICATIONS

Gallatin, et al., "A Cell–Surface Molecule Involved in Organ–Specific Homing of Lymphocytes," *Nature* (1983) 304:30–34.
Glabe, C.G. et al., "Preparation and Properties of Florescent Polysaccharides," *Anal. Biochem.* (1983) 130:287–294.
Stoolman and Rosen, "Possible Role for Cell–surface Carbohydrate–binding Molecules in Lymphocyte Recirculation," *J. Cell Biol.* (1983) 96:722–729.
Stoolman, L.M. et al., "Phosphomannosyl Receptors May Participate in the Adhesive Interaction between Lymphocytes and High Endothelial Venules," *J. Cell Biol.* (1984) 99:1535–1540.
Constantine–Paton, et al., "A Cell Surface Molecule Distributed in a Dorsoventral Gradient in the Perinatal Rat Retina," *Nature*, (1986) 324:459–462.
Brandley, et al., "Cell–Surface Carbohydrates in Cell Recognition and Response," *J. Leuk. Biol.*, (1986) 40:97–111.
Willenborg, D.O. and Parish, "Inhibition of Allergic Encephalomyelitis in Rats by Treatment With Sulfated Polysaccharides," *J. Immunol.* (1988) 140: 3401–3405.
Kishimoto, T.K., et al., Neutrophil Mac–1 and MEL–14 Adhesion Proteins Inversely Regulated by Chemotactic Factors,: *Science* (1989) 245:1238–1241.
Laskey, L.A., et al., "Cloning of a Lymphocyte Homing Receptor Reveals a Lectin Domain," *Cell* (1989) 56:1045–1055.
Siegelman, M.H., "Scientific Competency Through Fun," *Science* (1989) 243:1165–1177.
Willenborg, D.O. et al., "Phosphosugars are potent inhibitors of central nervous system inflammation," *FASEB J.* (1989) 3:1968–1971.
Kishimoto, T.K. et al., "Identification of a Human Peripheral Lymph Node Homing Receptor: A Rapidly Down–Regulated Adhesion Molecule," *Proc. Natl. Acad. Sci. USA* (1990) 87:2244–2248.
Springer, T.A., "Adhesion receptors of the immune system," *Nature* (1990) 346:425–434.
Spertini, O. et al., "Regulation of Leukocyte migration by activation of the leukocyte adhesion molecule–1 (LAM–1) selectin," *Nature* (1991) 349:691–694.
Watson, S.R. et al., "Neutrophil influx into an inflammatory site inhibited by a soluble homing receptor–IgG chimaera," *Nature* (1991) 349:164–167.
Mulligan et al., "Role of Endothelial–Leukocyte Adhesion Molecule 1 (ELAM–1) in Neutrophil–mediated Lung injury in Rats," *J. Clin. Invest.* vol. 88, pp. 1396–1406 (1991).
Mulligan et al., "Protective effects of oligosaccharides in P–selectin–dependent Lung injury," *Nature*, vol. 364.
Kansas et al., "A Role for the Epidermal Growth Factor–like Domain of P–Selectin in Ligand Recognition and Cell Adhesion," *J. Cell Biol.* 124:609–618 (1994).
Hales et al., "Labeled Antibodies and Their Use in the Immunoradiometric Assay," Methods in Enzymology (1980) 70:334–354.
Watson et al., *J. Cell Biol.* (1990) 110:2221–2229.
Lasky et al., *Cell* (1992)69:927–938.
Rudinger, "Peptide Hormones" University Park Press, Baltimore (Parsons et al., eds) pp. 1–7. (1976).

*Primary Examiner*—Christina Y. Chan
*Assistant Examiner*—Phillip Gambel
*Attorney, Agent, or Firm*—Bozicevic, Field & Francis; Bret Field

[57] ABSTRACT

The present invention provides novel assays for determining the ability of a test compound to inhibit intercellular adhesion mediated by a selectin receptor, such as the LHR. The assay involves coating a surface of a solid substrate with an antibody which specifically binds a selectin ligand. Preferred are antibodies against GlyCAM-1 which is a natural biological ligand for L-Selectin and also binds to P-Selectin and E-Selectin. A compound such as GlyCAM-1 is then bound to the antibodies. The test compound mixture putatively containing a selectin ligand is then brought into contact with a chimeric molecule. The test mixture might include any compound which might block or hinder binding between a selectin receptor and the ligand bound to the antibody. The chimeric molecule is comprised of an immunoglobulin bound to a selectin receptor and is introduced under conditions such that the selectin receptor portion of the chimeric molecule will bind to the selectin ligand bound to the antibodies on the surface if such binding is not blocked by the test compound. Bound chimeric molecules can be detected in a variety of ways such as by a conjugate compound of an anti-immunoglobulin antibody bound to enzyme such as alkaline phosphatase for the generation of color. Any test compounds which bind to the selectin receptor and block finding can be isolated, analyzed and identified.

9 Claims, 6 Drawing Sheets

Effect of PPME or Man6P on L-selectin/Ig binding to GlyCAM-1

ASSAYS FOR INHIBITORS OF LEUKOCYTE ADHESION

CROSS REFERENCE TO RELATED APPLICATIONS

This application is a continuation of application Ser. No. 08/425,362 filed on Apr. 18, 1995 and now abandoned, which application is a continuation in part of application Ser. No. 08/132,582 filed on Oct. 6, 1993, now abandoned, which application is a divisional of application Ser. No. 07/695,805 filed on May 6, 1991, now issued as U.S. Pat. No. 5,318,890, the disclosures of which are herein incorporated by reference.

GOVERNMENT RIGHTS

This invention was made in part, with support under Grant (or Contract) No. MIH GM-23547, awarded by the DHHS. The Government may have certain rights in this invention.

FIELD OF THE INVENTION

The present invention relates to methods for identifying compounds useful in the inhibition of cellular adhesion involved in a number of pathological responses and components used in such assays. In particular, the invention relates to assays for obtaining and isolating inhibitors of selectin receptors which are a class of receptors which mediate leukocyte extravasation and other responses.

BACKGROUND OF THE INVENTION

Recent work has established that specialized cell surface receptors (termed here selectins) on endothelial cells and various circulating cells are involved in a number of intercellular interactions. For instance, an adhesion molecule on the surface of leukocytes, lymphocyte homing receptor (LHR), is known to be involved in the adhesive interactions of leukocytes with the endothelial lining of blood vessels. This adhesive interaction is a prerequisite for the movement of leukocytes from the blood to tissue sites where immune reactions and inflammatory reactions occur.

LHR (also known as $gp90^{MEL}$, $gp100^{MEL}$, $gp110^{MEL}$, Mel-14 antigen, Leu8 antigen, TQ antigen, DREG antigen, LAM-1, selectin 1, LECAM-1, LEC-CAM-1, LEEK and L-Selectin depending on animal species, leukocyte, and laboratory preference) is expressed on the surface of leukocytes, such as, lymphocytes, neutrophils, monocytes, and eosinophils (Gallatin, et al., *Nature* 303:30 (1983) and Lewisohn, et al., *J. Immunol.* 138:4313 (1987), which are incorporated herein by reference). LHR is known to mediate the adhesion of lymphocytes to specialized endothelial cells in lymph nodes, leading to the migration of blood-borne lymphocytes into the lymph node. On neutrophils and monocytes, it mediates the early interaction of these cells with endothelium of blood vessels at sites of inflammation.

LHR is a lectin-like protein which performs its adhesive function recognizing carbohydrate-containing ligands on endothelial cells. Lectin-like receptors have also been found on endothelial cells and platelets. Endothelial leukocyte adhesion molecule-1 (ELAM-1) also known as CD62E and E-Selectin is present on endothelial cells and is involved in the recognition of various circulating cells by the endothelium. Granule membrane protein-140 (GMP-140) also known as CD62P and P-Selectin is present on the surface of platelets and endothelial cells, where it mediates platelet-leukocyte and endothelium-leukocyte interactions.

Recent work has established that these receptors share certain structural features. Each of the receptors in this class is a glycoprotein with a lectin-like domain, a region with homology to epidermal growth factor, and a region with homology to complement regulatory proteins (see, Springer, *Nature,* 346:425, 1989, which is incorporated herein by reference). The term "selectin" is used herein to refer to this class of lectin-like receptors.

There is currently an interest in developing highly specific competitive inhibitors of selectin-mediated cellular adhesion. Such inhibitors are useful in therapeutic regimens to treat various selectin-mediated disease responses. The inhibitors could also be used to target other pharmaceutical compounds, such as anti-inflammatory agents or anti-oxidants, to the sites of injury.

In view of the above it is important to improve our understanding of the interaction of selectin receptors and their ligands. Thus, it is important to develop rapid, economical methods for identifying inhibitors of selectin-mediated interactions. In the past in vitro intercellular adhesion assays have been used to test inhibition (see, e.g., Stamper and Woodruff, *J. Exp. Med.* 144:828–833 (1976), which is incorporated herein by reference). These assays, however, are difficult to carry out and do not lend themselves to screening large numbers of test compounds. Comparisons of active compounds by quantitative dose-response studies is difficult using these assays.

Previous ELISA's for L-selectin have measured its interaction with PPME, sulfatide, or $sLe^x$, Foxall, C., S. R. Watson, D. Dowbenko, C. Fennie, L. A. Lasky, M. Kiso, A. Hasegawa, D. Asa, and B. K. Brandley. (1992). The three members of the selectin receptor family recognize a common carbohydrate epitope, the sialyl $Lewis^x$ oligosaccharide. *J. Cell. Biol.* 117:895–902. Imai, Y., L. A. Lasky, and S. D. Rosen. (1992). Further characterization of the interaction between L-selectin and its endothelial ligands. *Glycobiology.* 2:373–381. Imai, Y., D. D. True, M. S. Singer, and S. D. Rosen. (1990). Direct Demonstration off the lectin activity of gp90MEL, a lymphocyte homing receptor. *J. Cell. Biol.* 111:1225–1232. The first two carbohydrates are fortuitous ligands, and their interaction with L-selectin reflects only limited features of the carbohydrate specificity of the lectin. $sLe^x$ is part of the endogenous ligands for L-selectin (see above), but without sulfate has very low affinity for L-selectin. The use of $sLe^x$ in an ELISA is thus problematic.

The present invention is a highly sensitive assay for finding compounds which inhibit interaction between a selectin receptor and a natural ligand. The present assay may be easily and efficiently carried out without the need for radioactive materials.

SUMMARY OF THE INVENTION

The present invention provides novel assays for determining the ability of a test compound to inhibit intercellular adhesion mediated by a selectin receptor, such as the LHR. The assay involves coating a surface of a solid substrate with an antibody which specifically binds a natural selectin ligand. Preferred are antibodies against GlyCAM-1 which is a natural biological ligand for L-Selectin and also binds to P-Selectin and E-Selectin. A compound such as GlyCAM-1 is then bound to the antibodies. The test compound mixture putatively containing a selectin ligand is then brought into contact with a chimeric molecule. The test mixture might include any compound which might block or hinder binding between a selectin receptor and the ligand bound to the antibody. The chimeric molecule is comprised of an immunoglobulin fused to a selectin receptor and is introduced under conditions such that the selectin receptor portion of the chimeric molecule will bind to the GlyCAM-1 bound to the antibodies on the surface if such binding is not blocked by the test compound. Bound chimeric molecules can be detected in a variety of ways such as by a conjugate compound of an anti-immunoglobulin antibody bound to enzyme such as alkaline phosphatase for the generation of color. Any test compounds which bind to the selectin receptor and block binding can be isolated, analyzed and identified.

The assays are typically carried out in a cell-free environment in which an antibody to GlyCAM-1 is immobilized on a solid surface and GlyCAM-1 is bound to the antibodies. The assays may also be performed by directly binding GlyCAM-1 or a related ligand-like molecule to the solid surface.

An object of the invention is to provide an assay method whereby ligands which bind to a selectin receptor (e.g., L-selectin, E-selectin or P-selectin) can be concentrated, isolated and/or identified.

An advantage of the invention is that it is highly sensitive and selective with respect to the detection of selectin inhibitors in a sample.

Another advantage is that the assay can be carried out without the use of radioactive materials.

A feature of the invention is that the assay uses a chimeric molecule comprised of an immunoglobulin fused to a selectin receptor.

These and other objects, advantages and features of the present invention will become apparent to those skilled in the art upon reading this disclosure.

DETAILED DESCRIPTION OF PREFERRED EMBODIMENTS

Before the present assay and method for using same is described, it is to be understood that this invention is not limited to the particular assay, chimeric molecule or methodology described as such assays, molecules and methods and its components may, of course, vary. It is also to be understood that the terminology used herein is for the purpose of describing particular embodiments only and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a substrate surface" includes a plurality of different surfaces such as a plurality of beads, reference to "an antibody" includes a plurality of antibodies and mixtures thereof and reference to "the receptor" includes a plurality of receptors of the type generally described herein.

Unless defined otherwise all technical and scientific terms used herein have the same meaning as commonly understood by one of ordinary skill in the art to which this invention belongs. Although any methodology and materials similar or equivalent to those described herein can be used in the practice or testing of the present invention, the preferred methods and materials are now described. All publications mentioned herein are incorporated herein by reference for the purpose of disclosing and describing the particular materials and methodologies for which the reference was cited in connection with.

The present invention provides novel assays useful in identifying inhibitors of selectin-mediated intercellular adhesion. Also provided is chimeric molecule comprised of an immunoglobulin bound directly or indirectly to a selectin receptor.

Figure 5:
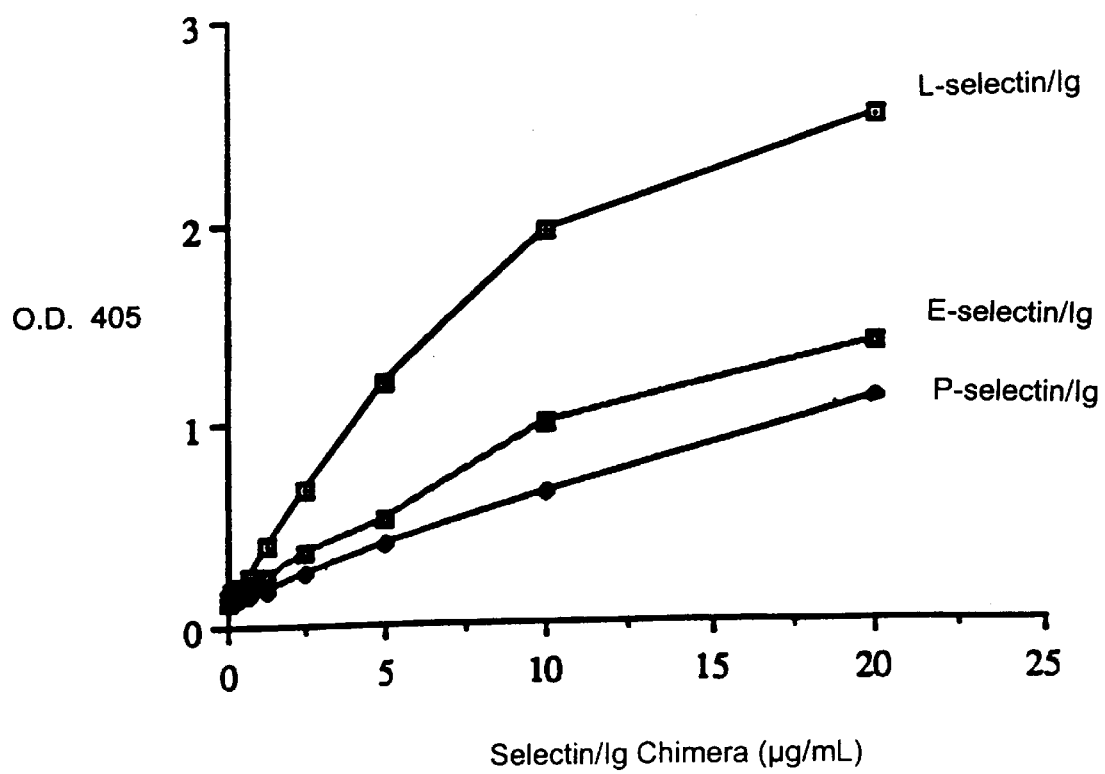
FIG. 5 is a graph showing results with assays of the invention with different selectin receptors.

Although assays of the present invention can be configured in a number of ways it is preferable to provide an ELISA assay configuration in that ELISA assays are generally familiar to those skilled in the art and include components which are commercially available. The assays of the invention provide a sensitive, non-radioactive means to compare carbohydrates of defined structure against any given selectin, e.g., the three selectins as per FIG. 5. The assay is also suitable for screening of chemical and natural product libraries, because it is highly sensitive and has the potential of very high throughput. A further advantage over previously described assays is that GlyCAM-1 is an actual biological ligand for L-selectin. Thus, the assay may allow the identification of important inhibitors that would be missed with assays based on fortuitous (e.g., PPME, fucoidin) or incomplete (e.g., sulfatide, sLe$^x$) carbohydrate ligands.

Figure 1:
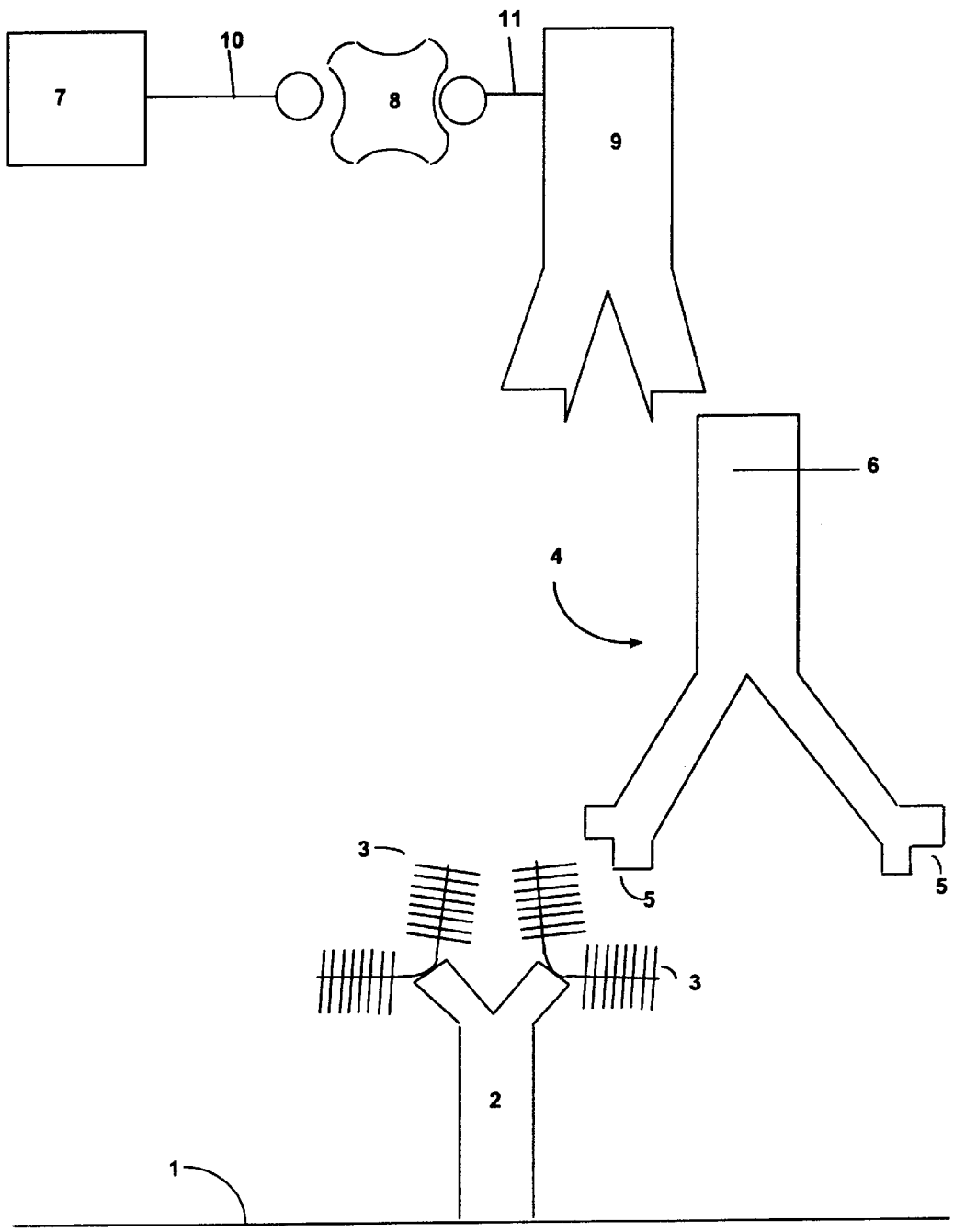
FIG. 1 is a schematic view of a preferred embodiment of the assay of the invention.

FIG. 1 schematically shows the assay of the invention. The preferred embodiment is comprised of a support surface 1 which is preferably an ELISA well surface. An antibody 2 is bound to the support 1 and is an antibody which preferentially binds to a selectin ligand, e.g., GlyCAM-1. The antibody 2 need not be present to operate the assay of the invention. However, use of the antibody 2 greatly facilitate the production of the assay in that the antibody 2 is used to bind to and hold molecules 3 (such as GlyCAM-1) in place.

Once the molecules 3 are held in place any excess material or molecules 3 are removed by appropriate washing. There are at least two alternates for carrying out the invention at this point. (1) A composition which putatively contains a selectin binding compound is added together with a chimeric molecule 4 comprised of a selectin portion 5 (which is preferably L-selectin, E-selectin or P-selectin) bound to an immunoglobulin portion 6 (which is preferably the Fc portion of human IgG). (2) The chimeric molecule 4 is mixed with a compound which putatively blocks a selectin receptor and the mixture is contacted with the molecules 3 bound to antibody 2 on support 1. The chimeric molecule 4 is preferably genetically produced as a dimer which includes both the receptor 5 and immunoglobulin 6 portions.

If no compound binds to the receptors the receptor 5 will bind to the molecule 3. Binding of the receptor 5 to the molecule 3 can be detected and the degree to which that binding is blocked can be determined.

The receptor 5 is fused to an immunoglobulin 6 to form the chimeric molecule 4. The chimeric molecule is preferably connected to a detectable label 7. The connection may be direct but is generally via a number of compounds. For example, the label 7 may be connected to streptavidin 8 which is connected to a composition 9 (such as biotinylated anti-human (Fc)) which selectively binds to the immunoglobulin portion 6 of the chimeric molecule 4. The label 7 may be directly connected to the streptavidin 8 or connected via a linking group 10 which is preferably biotin to which streptavidin binds. The streptavidin may be directly connected to the composition 9 or connected via a linking group 11 which is preferably the biotin of biotinylated anti-human Fc shown as 9 in FIG. 1.

Figure 2:
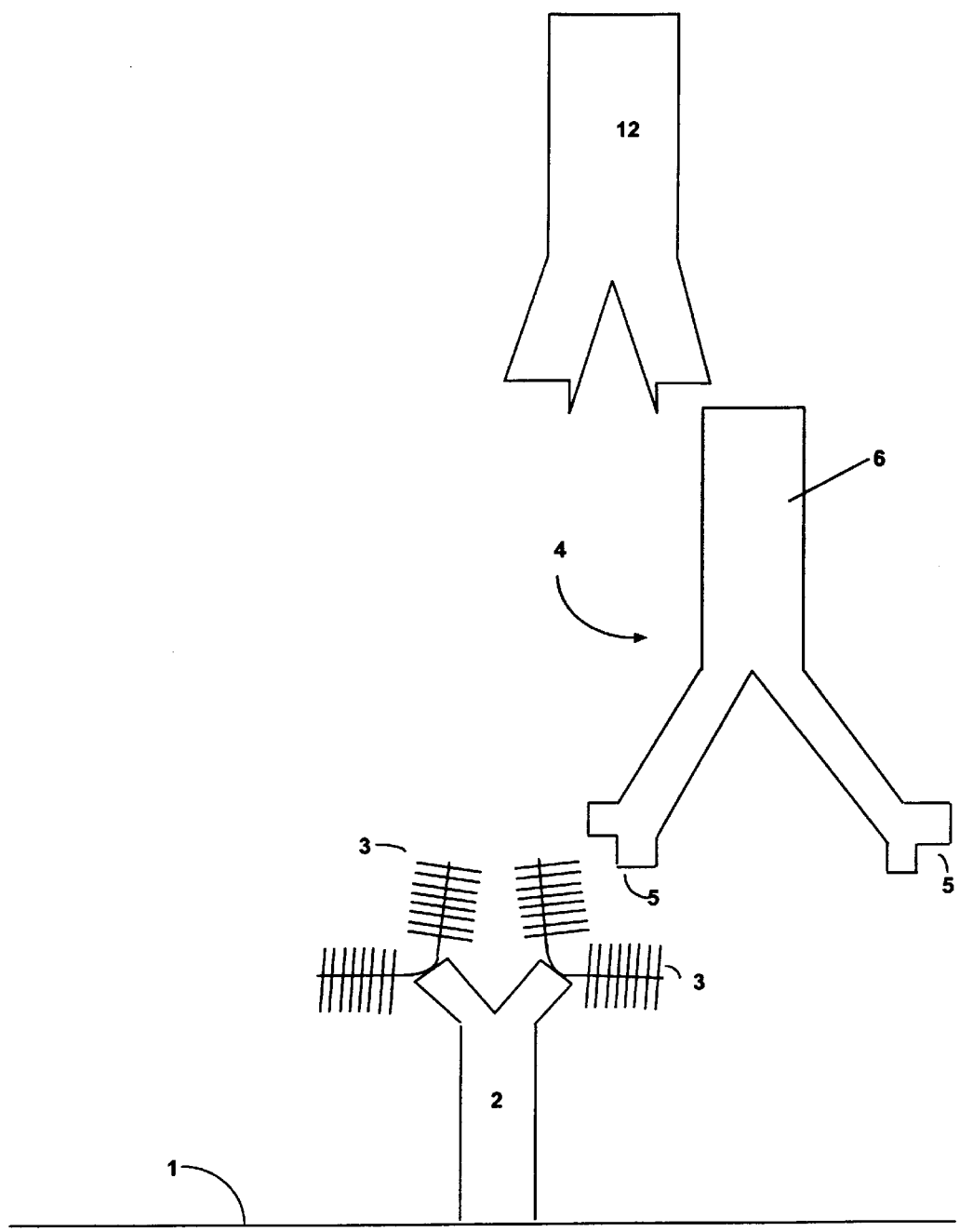
FIG. 2 is a schematic view of a simple embodiment of the assay of the invention.

FIG. 2 shows an assay with less components. The antibody 2 is bound to a support 1 and ligand molecule 3. The assay works by testing the ability of a given compound to block or hinder binding between the compound 3 and a receptor 5 of a chimeric molecule 4 which also includes an immunoglobulin portion 6. Any suitable detectable label 12 which can be attached is connected to the chimeric molecule 4.

Figure 3:
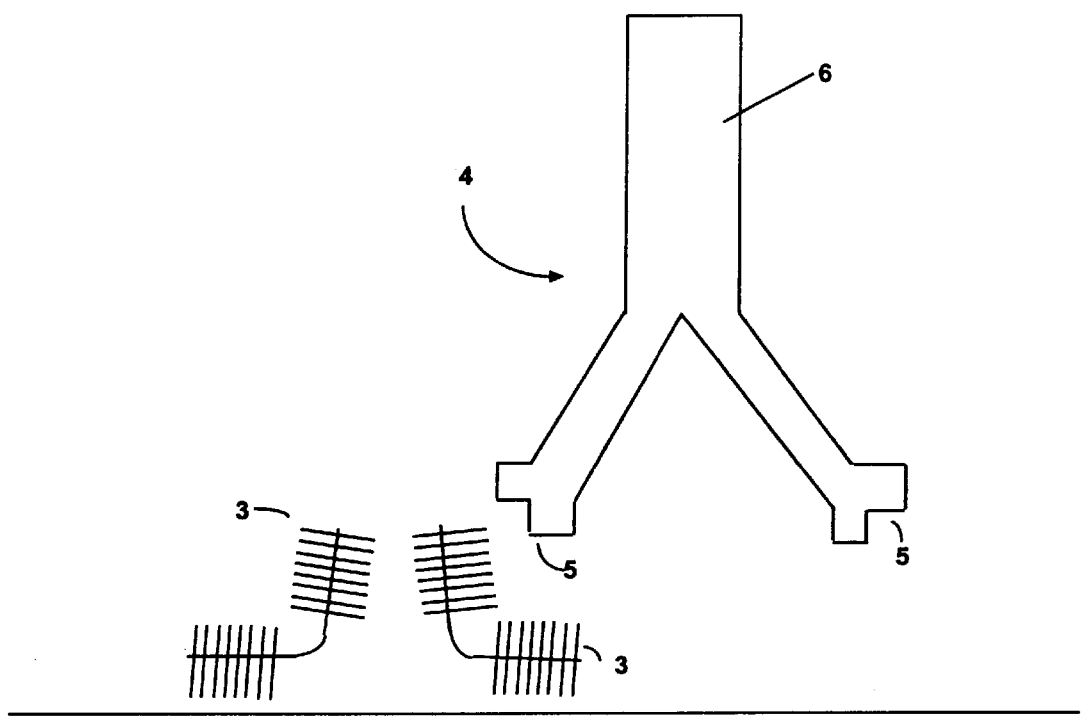
FIG. 3 is a schematic view of the simplest embodiment of the assay of the invention.

FIG. 3 is a schematic view of the essential components of an assay of the invention. The molecules 3 which are known to bind to a given receptor 5 are bound to the support 1 directly; i.e., without the use of an antibody 2 a per FIGS. 1 and 2. Many molecules 3 such as GlyCAM-1 are difficult to purify and/or cannot be easily bound to a surface 1 thus requiring the antibody link for the connection.

In a preferred embodiment a ligand is purified from serum or other body fluid using an antibody for that ligand. In particular it is useful to partially purify GlyCAM-1 from mouse serum with a chloroform-methanol step. The GlyCAM-1 is captured on microtiter wells by an affinity-purified antibody to GlyCAM-1. The bound GlyCAM-1 is then detected with the L-selectin/Ig chimera in a complex with biotinylated goat-anti human antibody/streptavidin/ alkaline phosphatase (the pre-formation on this complex is essential for high-sensitivity detection).

In FIG. 3 the molecules 3 which are directly attached to the surface 1 are preferably neoglycoligands or neoglycoproteins, more preferably GlyCAM-1, and the receptor 5 is one which binds selectively to such compounds. In order to observe the results obtained with the assay of FIG. 3 it is preferable to attach some detectable label (at some location and point in time) to the immunoglobulin portion 6 of the chimeric molecule 4.

Figure 4:
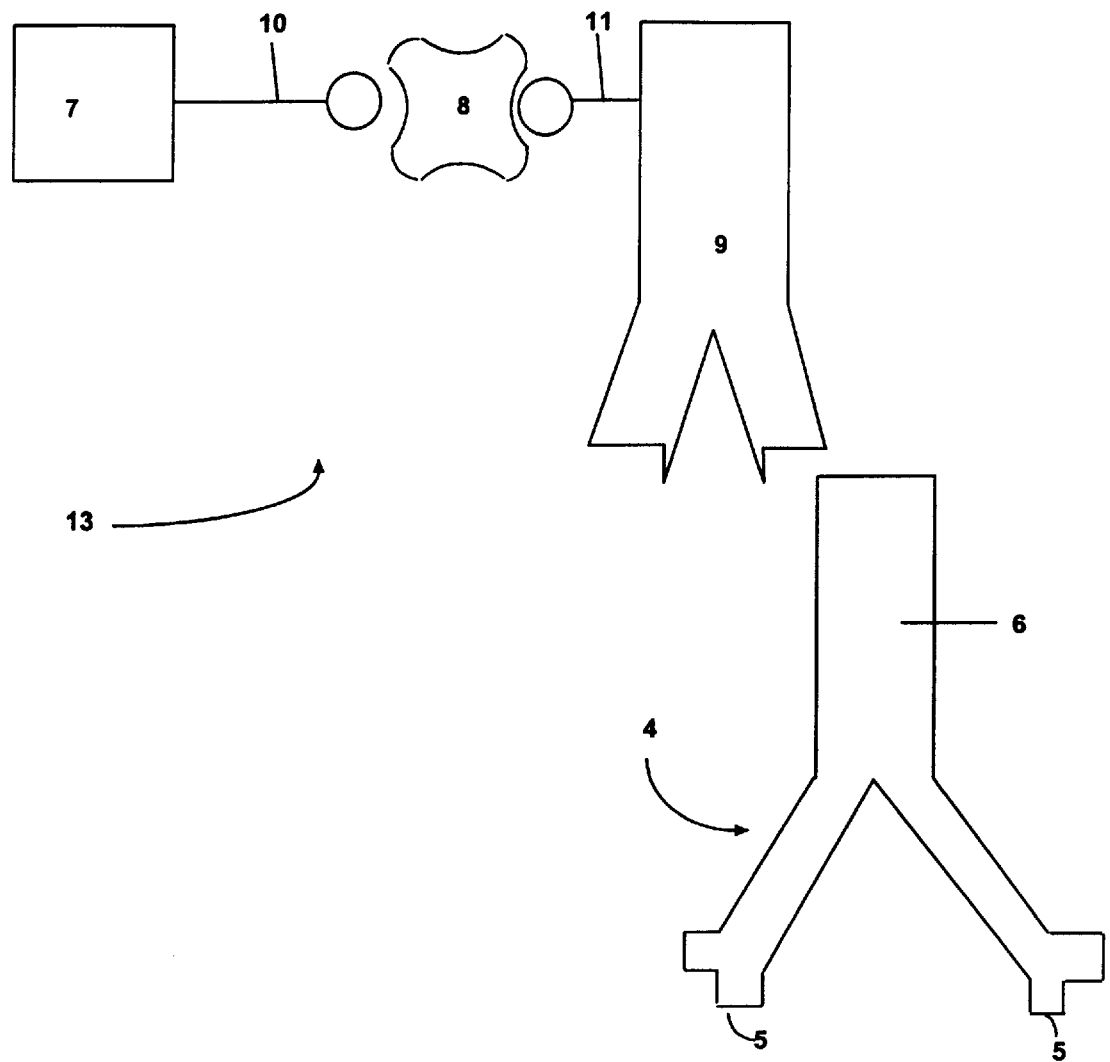
FIG. 4 is a schematic view of a preferred embodiment of a chimeric molecule of the invention.

FIG. 4 shows a detectable attaching unit (DAU) 13 by itself which is considered to be an aspect of the present invention. The DAU 13 is comprised of a chimeric molecule 4 (which includes selectin receptor 5 and immunoglobulin component 6), composition 9 (which binds to the immunoglobulin component 6) and label 7. The label 7 includes an attachment group 10 and the composition 9 includes a similar attachment group 11. Attachment groups 10 and 11, preferably biotin, are joined by an interconnecting component 8, preferably avidin or streptavidin. Different forms of DAUs can be created, e.g., with different selectin receptors 5 to meet the needs of the particular researcher Selectin Receptors The term "selectin receptor" as used herein is intended to broadly encompass molecules of the type described below and their functional equivalents which bind to ligands involved in the inflammatory response. Preferred selectins are L-selectin (CD62L), E-selectin (CD62E) and P-selectin (CD62P). The selectin receptor is formed as the receptor 5 portion of the chimeric molecule 4 along with the immunoglobulin component 6. Preferably, the chimeric molecule 4 is composed of two receptor 5 portions, each of which can bind molecule 3.

Selectins, or selectin receptors also known as the "LEC-CAM" family of cell adhesion molecules, are unique cell surface glycoproteins. These receptors are involved in a variety of intercellular interactions and are generally referred to as lymphocyte homing receptors (LHR). For instance, the trafficking of lymphocytes from the blood into secondary lymphoid organs, such as lymph nodes and gut-associated Peyer's patches, is known to be initiated by an adhesive interaction between specialized endothelial cells of high endothelial venules (HEV) and LHRs on lymphocytes. Berg, et al., *Immuol. Rev.* 108:5–18 (1989); Duijvestijn and Hamann, *Immunol. Today* 10:23–28 (1989); Woodruff, et al., *Ann. Rev. Immunol.* 5:201–222 (1987); Yednock and Rosen, *Adv. Immunol.* 54:313–378 (1989); Stoolman, *Cell* 56:907:910 (1989); Gallatin, et al., *Cell* 44:673–680 (1986); Rosen, *Curr. Opin. Cell. Biol.* 1:913–919 (1989), all of which are incorporated herein by reference.

The selectin receptor used to form the chimeric molecule of the present invention may or may not be associated with an intact cell. Typically, the receptor is purified from its native environment before use in the assay. As discussed above, cDNA encoding each of the selectin receptors has been isolated. Thus, the receptors can be recombinantly produced using standard methods well known to those skilled in the art. For a review of standard molecular biological techniques see Sambrook, et al., *Molecular Cloning: A Laboratory Manual,* 2d Ed. (Cold Spring Harbor Press, N.Y., 1989), which is incorporated herein by reference. In addition, using standard recombinant DNA techniques, mutations (or dimers which form the chimeric molecule 4) can be induced to obtain proteins with altered amino acid sequences. Typically, substitutions, deletions or additions are introduced which provide desired characteristics. For instance, increased solubility can be achieved by elimination of the hydrophobic transmembrane region of the protein. In addition, soluble chimeric receptors comprising the constant region of an immunoglobulin molecule can also be produced (Watson, et al., *J. Cell Biol.* 110:2221–2229 (1990), and Watson, et al., *Nature* 349:164–167 (1991) which are incorporated herein by reference).

The endothelial ligands recognized by LHR molecules are postulated to be distinctive for the different lymphoid organs and as such are proposed to be responsible for regulating the lymphocyte populations that enter each class of lymphoid organ. Strong support for organ-specific HEV determinants has come with the discovery of the mouse "vascular addressin" antigens, defined by the panel of MECA monoclonal antibodies (Streeter, et al., *Nature* 331:41–46 (1988) and Streeter, et al., *J. Cell. Biol.* 107:1853–1962 (1988) both of which are incorporated herein by reference).

The lectin domain on LHR for lymph nodes in humans and mice was initially inferred based upon the ability of specific phosphorylated monosaccharides, such as mannose-6-phosphate (M6P), and specific polysaccharides to prevent lymphocyte attachment to HEV (Stoolman and Rosen, *J. Cell Biol.* 96:722–729 (1983); Stoolman, et al., *J. Cell Biol.* 99:1535–1540 (1984); Yednock, et al., *J. Cell Biol.* 104;713–723 (1987); Stoolman, et al., *Blood* 70:1842–1850 (1987); Stoolman and Ebling, *J. Clin. Invest.* 84:1196–1205 (1989) all of which are incorporated herein by reference). Notable among the active polysaccharides are PPME (a phosphate-rich mannan core) and fucodin (a sulfated, fucose-rich polymer). This carbohydrate-binding activity depends on the presence of calcium, which is also required for the attachment of lymphocytes to HEV.

From the lectin nature of LHR, the ligands on lymph node HEV are presumed to bear a carbohydrate-based recognition determinant. Early studies demonstrated that the adhesive sites on peripheral lymph node HEV are periodate sensitive (Rosen, et al., *Science* 228:1005–1007 (1985) which is incorporated herein by reference), indicating a requirement for carbohydrate. Subsequently, it was demonstrated that sialidase treatment of HEV, in vitro or in vivo, selectively eliminates lymphocyte attachment to peripheral lymph mode HEV but has no effect on the binding to Peyer's patch HEV (Rosen, et al., *J. Immunol.* 142:1895–1902 (1989) which is incorporated herein by reference). In addition, exposure of peripheral lymph node tissue sections to Limax flavus agglutinin, a sialic acid-specific lectin, prevents lymphocyte attachment to HEV (True, et al., *J. Cell Biol.* 111:2757–2764 (1990) which is incorporated herein by reference.

The biochemical nature of the ligands, however, has only been partially defined. Adhesion-blocking activity and selective staining of peripheral lymph node HEV have been shown by MECA-79, a monoclonal antibody which recognizes a complex of HEV cell surface proteins (EPO Publication No. 0303463 and Butcher, *Am. J. Pathol.* 136:3–12 (1990) which are incorporated herein by reference). The LHR specifically binds a natural surface glycoprotein or a compatible test compound which compound will bind to this antibody. The LHR recognizes a sulfated, fucosylated and sialylated glycoprotein of about 50 kd now termed GlyCAM-1. A glycoprotein of 90 kd (now known as CD34) with similar characteristics is also identified. The present assay can abe used to find additional compounds which will bind to LHR.

Other selectins have also been extensively studied. ELAM-1 or E-selectin is inducibly expressed on vascular endothelial cells (Bevilacqua, et al., *Science* 243:1160 (1989) and Hession, et al., *Proc. Nat'l. Acad. Sci.,* 87:1673–1677 (1990), both of which are incorporated herein by reference). This receptor has been demonstrated to be induced by inflammatory cytokines such as interleukin I$\alpha$ (IL-I$\beta$) and tumor necrosis factor $\alpha$ (TNF$\alpha$), as well as bacterial endotoxin (lipopolysaccharide) (see, Bevilacqua, et al., *Proc. Natl. Acad. Sci.,* 84:9238–9242 (1987) which is incorporated herein by reference). These compounds act directly on endothelial cells in vitro to substantially augment polymorphonuclear leukocyte (neutrophil), and monocyte adhesion (Bevilacqua, et al., *Proc. Natl. Acad. Sci.,* supra). Detailed structures have been proposed for an oligosaccharide moiety recognized by ELAM-1 (Phillips, et al., *Science* 250:1130–1132 (1990) and Walz, et ala., *Science* 250:1132–1135 (1990), both of which are incorporated herein by reference.

A third member of the selectin family, GMP-140 or P-selectin, is a membrane glycoprotein of platelet and endothelial secretory granules (Geng, et al., *Nature.* 343:753–760 (1990) which is incorporated herein by reference). Activated platelets which express GMP-140 on their surface are known to bind to monocytes and neutrophils (Jungi, et al., *Blood* 67:629–636 (1986), and also to monocyte-like cell lines, e.g., HL60 and U937 (Jungi, et al., supra; Silverstein, et al., *J. Clin. Invest.* 79:867–874 (1987)), all of which are incorporated herein by reference). P-selectin is an alpha granule membrane protein of molecular weight 140,000 that is expressed on the surface of activated platelets upon platelet stimulation and granule secretion (Hsu-Lin, et al.,*J. Biol. Chem.* 259:9121–9126 (1984); Steinberg, et al.,*J. Cell Biol.* 101:880–886 (1985); Berman, et al., *J. Clin. Invest.* 78:130–137 (1986)). It is also found in megakaryocytes (Beckstead, et al., *Blood* 67:285–293 (1986)), and in endothelial cells (McEver, et al.,*Blood* 70:355a (1987)) within the Weibel-Palade bodies (Bonfanti, et al.,*Blood* 73:1109–1112 (1989))). Furie, et al., U.S. Pat. No. 4,783,330, describe monoclonal antibodies reactive with GPM-140. All of the foregoing references are incorporated herein by reference.

The structure and function of selectin receptors has been elucidated by cloning and expression of full length cDNA encoding each of the above receptors (see, e.g., Bevilacqua, et al., *Science, surra,* (ELAM-1), Geng, et al., supra, (P-selectin), and Lasky, et al., *Cell* 56:1045–1055 (1989) (LHR) which is incorporated herein by reference). The extracellular portion of selectins can be divided into three segments based on homologies to previously described proteins. The N-terminal region (about 120 amino acids) is related to the C-type mammalian lectin protein family as described by Drickamer, *J. Biol. Chem.,* 263:9557–9560 (1988) (which is incorporated herein by reference) that includes low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins. Immunoglobulin The immunoglobulin component 6 of the chimeric molecule 4 is preferably the Fc portion of IgG but may be all or any functional part of any immunoglobulin component. This portion of the chimeric molecules 4 should be of a type that it can be produced along with the selectin receptor portion and can be used to attach other components needed to generate a signal. In general the DNA for immunoglobulin and its components are known and can be used with the DNA encoding a selectin receptor to provide the chimeric molecule 4 of the invention.

Immunoglobulins are antibodies secreted by mature lymphoid cells called plasma cells. Immunoglobulins are Y-shaped tetrameric molecules consisting of two relatively long peptide chains called heavy (H) chains and two shorter polypeptide chains called light (L) chains. Each arm of the Y-shaped structure has specific antigen-binding properties and is referred to as an antigen-binding fragment (Fab). The tail of the Y-structure is crystalizable fragment (Fc). Five H chain classes of immunoglobulin are based upon their antigenic structures. Immunoglobulin class G(IgG) is the most common in serum and is associated with immunological "memory"; class IgM is the earliest to appear upon initial exposure to an antigen. Class IgA can be secreted across epithelial tissues and seems to be associated with resistance to infectious diseases of the respiratory and digestive tracts. The antibodies associate with immunological allergies belong to class IgE. Not much is known about the functions of IgD. Antibodies of classes IgG, IgD, and IgE have molecular weights ranging from between 150,000–200,000d (7S); serum IgA is a 7S monomer, but secretory IgA is a dimer (11.4S); IgM is a pentamer (19S; 900,000d) of five 7S-like monomers.

The immunoglobulin component 6 is preferably Fc of IgG because it is readily available and binds well to anti-human Fc (component 9) which is also readily available.

Immunoglobulin genes are known which encode the light and heavy chains of immunoglobulins. These genes are remarkable in that they are made up of segments that are shuffled as the B lymphocytes mature. The light chains contain segments that can be symbolized L-V, J and C. The V or variable segment codes for the first 95 amino acids of the chain, whereas the C or constant segment codes for amino acids 108 to 214. The joining segment, J, codes for amino acids 96 to 107. L codes for a leader sequence 17–20 amino acids long. It functions in the transport of the molecule through the plasmalemma and is cleaved off the molecule process. There are about 300 L-V segments per light chain gene, and each of the V segments has a different base sequence. In the kappa gene there are six J segments, each with a different base sequence, and one C segment. During differentiation of a given B lymphocyte stem cell, an immunoglobulin gene is assembled containing one L-V, one J, and one C segment, and this gene is transcribed by the lymphocyte and all of its progeny. The lambda gene also contains about L-V segments, but each of the six J segments has its sown adjacent C segment. The heavy chain gene is over 100,000 nucleotides long and contains a series of segments that can be symbolized L-V, D, J, $C_\mu$, $C_\delta$, $C3_\gamma$, $C_{\gamma 1}$, $C_{\gamma 2b}$, $C_{\gamma 2a}$, $C_\epsilon$, and $C_\alpha$. There are about 300 L-V segments, 10–50 D segments, 4 J segments, and one each of the c segments. Each D segment codes for about 10 amino acids. During differentiation the segments are shuffled so that the variable region of a heavy chain is encoded by a segment that contains one L-V, one D, and one J segment. The gene also contains mu, delta, gamma, epsilon, and alpha subsegments, and which one of these is transcribed determines the class to which the antibody will belong.

Chimeric Molecules

Chimeric molecules 4 used in assays of the present invention are comprised of a selectin receptor 5, preferably two selectin receptors 5, or functional portions thereof bound to an immunoglobulin 6 or functional portion thereof. The selectin receptor may be an amino acid sequence bound directly or via a linking molecule to the immunoglobulin of a portion thereof e.g., the Fc component. The receptor and immunoglobulin are preferably produced together as a dimer. Methods of producing such dimers are known as are methods of binding to either the N-terminal or carboxyl terminal of the receptor directly or via a suitable linking molecule are known to those skilled in the art. The chimeric molecule may include several selectin receptors attached to one immunoglobulin (e.g., 2–10 selectins) and may include several immunoglobulins (2–10) attached to one or more selectin receptors. Preferably two selectin receptors are attached to one immunoglobulin.

Assays—Advantages

As shown and described above assays of the present invention can provide a sensitive, non-radioactive means to compare carbohydrates of defined structure against all three selectins. The assay is also suitable for screening of chemical and natural product libraries, because it is highly sensitive and has the potential of very high throughput. A further advantage over previously described assays is that GlyCAM-1 is an actual biological ligand for L-selectin. Thus, the assay may allow the identification of important inhibitors that would be missed with assays based on fortuitous (e.g., PPME, fucoidin) or incomplete (e.g., sulfatide, sialyl $Le^x$ carbohydrate ligands. In this regard, it is noteworthy that a number of studies indicate that selectins may use additional interactions besides their carbohydrate binding activities to bind their biological ligands. There is published evidence for the importance of protein-protein interactions in selectin-ligand binding, Siegelman, M. H., Cheng, I. C., Weissman, I. L., and Wakeland, E. K., (1990). The mouse lymph node homing receptor is identical with the lymphocyte cell surface marker Ly-22: Role of the EGF domain in endothelial binding. *Cell* 61:611–622. Kansas, G. S., Saunders, K. B., Ley, K., Zakrzewicz, A., Gibson, R. M., Furie, B., and Tedder, T. F., (1994). A role for the epidermal growth factor-like domain of P-selectin in ligand recognition and cell adhesion. *J. Cell. Biol.* 124:609–618. The new ELISA based on GlyCAM-1 can thus potentially detect new inhibitors that disrupt these protein-protein interactions as well as those that disrupt protein-carbohydrate interactions.

The present assay can greatly facilitate the isolation and/or identification of binding compounds which possess the ability to inhibit selectin-mediated responses. Ideally, the assays of the present invention allow large scale in vitro screening of a variety of compounds. Detection is carried out with the use of immunoglobulins and without the need for radioactive materials. Assays involving immunoglobulins are known (see, e.g., U.S. Pat. Nos. 3,376,110, 4,016,043 and Harlow and Lane, *Antibodies: A Laboratory Manual*, Cold Spring Harbor Publications, New York (1988), which are incorporated herein by reference).

The in vitro assays of the present invention are typically assays which detect the ability of a test compound to block or hinder binding to a ligand attached to an antibody. Antibodies can be generated using intact cells which express ligand molecules recognized by selectin receptors. However, antibodies are generally prepared using receptor-binding agents prepared from appropriate cells according to standard methods, purchased in a purified state, or synthetically produced. Although the agents are not associated with intact cell membranes they may be associated with cell membrane fragments or incorporated into artificial lipid membranes (e.g., liposomes).

Unlike prior art methods, the present assays are not based on measuring the presence or absence of intercellular adhesion but are typically carried out in a cell-free environment. The term "a cell-free environment" is used here to indicate that intact cells are substantially absent from the assay. The assay is considered to be cell-free despite the presence of cellular debris or cell membrane fragments which may be present in the test compound mixture.

The assay can be used to determine the degree to which a given compound can block or hinder binding between a natural selectin receptor and a natural ligand.

In the section below entitled "Solid Substrate Surface" there is provided a detailed description of methods of covalently and non-covalently binding biomolecules including antibodies and portions thereof to a surface. Any of such methods may be used in this invention.

Utility

Test compounds and mixtures thereof to be screened will usually be a synthetic or naturally-produced biomolecule, such as a carbohydrate (e.g., oligosaccharide) or glycoconjugate. Such compounds can also be peptides, polypeptides, proteins, nucleic acids, and the like. The test compound is typically a relatively small molecule with a molecular weight less than about 10 kFD, preferably less than about 5 kD. The compounds are synthetically produced using standard methods for synthesizing oligosaccharides (Khadem, supra). Methods for synthesizing polypeptides of defined composition are well known in the art (see, Atherton, et al., *Solid Phase Peptide Synthesis* (IRL Press, Oxford, 1989) which is incorporated herein by reference). If the synthetic test compounds are polymeric (e.g.. polypeptides or polysaccharides) they are preferably altered in a systematic way to identify the sequence of monomers which have the desired effect (see, e.g., U.S. Pat. No. 4,833,092, which is incorporated herein by reference). Test compounds may also be isolated from any natural source, such as animal, plant, fungal, or prokaryotic cells in accordance with standard procedures.

The assays of the present invention are particularly useful in identifying compounds which act as antagonists of a ligand molecule. Antagonists are compounds which reverse the physiological effect of a ligand or exclude binding of the ligand to the receptor. An antagonist competes directly or indirectly with the ligand for the receptor binding site and, thus, reduces the proportion of ligand molecules bound to the receptor. Typically, an antagonist will be the topographical equivalent of the natural ligand and will compete directly with the ligand for the binding site on the selectin. Such a compound is referred to here as a "mimetic". A ligand mimetic is a molecule that conformationally and functionally serves as substitute for the natural ligand recognized by a selectin receptor. Alternatively, if the ligand and the test compound can bind the receptor simultaneously, the compound may act non-competitively. A non-competitive inhibitor acts by decreasing or inhibiting the subsequent physiological effects of receptor-ligand interactions rather than by diminishing the proportion of ligand molecules bound to the receptor.

The in vivo utility of compounds which block selectin receptor in the treatment of inflammation has been established. For example, see Mulligan, et al., "Role of Endothelial-Leukocyte Adhesion Molecule 1 (ELAM-1) In Neutrophil-mediated Lung injury in Rats, " *J. Clin. Invest.* Volume 88, pages 1396–1406 (October 1991) and Mulligan, et al., "Protective effects of Oligosaccharides in P-selectin-dependent lung injury," *Nature,* Vol. 364, pages 149–151 (Jul. 8, 1993), both of which are incorporated by reference to provide an example of the utility of compounds which may be found using the assay of the present invention.

The assays of the present invention can also be used to identify synthetic or naturally occurring agonists. Agonists are compounds which bind the receptor and initiate a physiological response similar to that of the natural ligand. Such an agonist could be bound to leukocyte.

The inhibitors of selectin-ligand interaction identified by the assays of the present invention are useful in treating a number of selectin-mediated disease responses. For instance, selectins play an important role in recruitment of leukocytes to the sites of injury, particularly inflammation. The inhibitors therefore may be administered locally or systemically to control tissue damage associated with such injuries. Moreover, because of the specificity of such inhibitors for sites of inflammation, these compositions will be more effective and less likely to cause complications when compared to traditional anti-inflammatory agents.

Pharmaceutical compositions comprising the inhibitors can be used to block or inhibit cellular adhesion associated with a number of disorders. For instance, a number of inflammatory disorders are associated with selectins expressed on vascular endothelial cells and platelets. The term "inflammation" is used here to refer to reactions of both the specific and non-specific defense systems. A specific defense system reaction is a specific immune system reaction to an antigen. Examples of specific defense system reactions include antibody response to antigens, such as viruses, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of PMN leukocytes at sites of bacterial infection (e.g., pulmonary infiltrates in bacterial pneumonias and pus formation in abscesses).

Other treatable disorders include, e.g., rheumatoid arthritis, post-ischemic leukocyte-mediated tissue damage (reperfusion injury), frost-bite injury or shock, acute leukocyte-mediated lung injury (e.g., adult respiratory distress syndrome), asthma, traumatic shock, septic shock, and acute and chronic inflammation, including atopic dermatitis, psoriasis, and inflammatory bowel disease. Various platelet-mediated pathologies such as atherosclerosis and clotting can also be treated. In addition, tumor metastasis can be inhibited or prevented by inhibiting the adhesion of circulating cancer cells. Examples include carcinoma of the colon and melanoma.

Thus, the present invention also provides an assay useful in producing pharmaceutical compositions which can be used in treating the aforementioned conditions. The pharmaceutical compositions can be prepared according to standard methods (see *Remington's Pharmaceutical Sciences,* Mack Publishing Co., Philadelphia, Pa., 19th ed. (1985) which is incorporated herein by reference). The pharmaceutical compositions are suitable for use in a variety of drug delivery systems. For a brief review of present methods for drug delivery, see, Langer, *Science* 249:1527–1533 (1990), which is incorporated herein by reference.

In one embodiment, the inhibitors can be used to target conventional anti-inflammatory drugs or other agents to specific sites of tissue injury. (See U.S. Pat. No. 5,211,937 incorporated by reference). By using a selectin-binding moiety to target a drug to a selectin receptor on, e.g., a vascular endothelial cell, such drugs can achieve higher concentrations at sites of injury. Side effects from the conventional anti-inflammatory agents can be substantially alleviated by the lower dosages, the localization of the agent at the injury sites and/or the encapsulation of the agent prior to delivery. Targeting can be achieved by directly or indirectly linking the inhibitor to the anti-inflammatory agent. For instance, liposomes filled with the anti-inflammatory agent can be constructed which incorporate the inhibitor in the lipid membrane (see, Langer, supra). When the liposomes are brought into proximity of the affected cells, they deliver the elected therapeutic compositions.

The pharmaceutical compositions containing the inhibitors can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective dose." Amounts effective for this will, of course, depend on the severity of the disease and the weight and general state of the patient.

In prophylactic applications, compositions containing the inhibitors are administered to a patient susceptible to or otherwise at risk of a particular disease. Such an amount is defined to be a "prophylactically effective dose." In this use, the precise amounts again depend on the patient's state of health and weight.

Specific Assays

In a particularly preferred embodiment of the assay the substrate material is comprised of a synthetic polymeric material such as polyethylene, polypropylene or polystyrene. Specific ELISA wells are constructed of the polymeric material. Thereafter, antibodies or a biologically functional portion thereof are bound to the surface (non-covalently) of the polymeric materials. Any antibody portion must maintain its ability to selectively bind a selectin ligand. The antibodies are most preferably antibodies against GlyCAM-1.

An assay of the present invention may be structured as follows: SUBSTRATE-ANTIBODY-LIGAND COMPOUND-CHIMERIC MOL. The chimeric molecule is comprised of a selectin receptor (e.g., L-selectin) bound to an immunoglobulin or a biologically active portion thereof e.g., Fc of human IgG. The immunoglobulin is preferably bound to an enzyme for use in color detection. The chimeric molecule may be structured as follows: SELECTIN RECEPTOR-IMMUNOGLOBULIN-ENZYME. The connecting bonds may be indirect (via a linking group) but are preferably direct.

In order to test the antibodies, GlyCAM-1 which is extracted and isolated from serum (e.g., mouse or an animal including human sera) is coated onto the surface of the antibodies where the GlyCAM-1 will bind to the antibodies. GlyCAM-1 is an actual naturally occurring biological ligand for L-selectin and is a compound which inhibits intercellular adhesion mediated by a selectin receptor. It is a particularly well characterized compound of that class. After the GlyCAM-1 has been allowed to bind to the antibodies coated on the ELISA wells under appropriate binding conditions and excess unbound materials has been washed away the GlyCAM-1 is brought into contact with a chimeric molecule which is comprised of L-selectin non-covalently bound to biotinylated immunoglobulin. The L-selectin will bind to the GlyCAM-1. In order to detect the presence of a chimeric molecule bound to the GlyCAM-1 an enzyme such as alkaline phosphatase linked to streptavidin is added for the generation of color.

A number of known detection compositions can be used in connection with the assay. However, it is desirable to eliminate the use of radioactive materials and to use commercially available enzyme materials which generate color e.g., alkaline phosphatase. The use of such improves the efficiency, reduces costs and eliminates the use of undesirable dangerous radioactive materials.

The detecting agent alkaline phosphatase, catalyzes the hydrolysis of p-nitrophenyl phosphate to p-nitrophenol, a substance with a visible absorption max of 405 nm. The presence of p-nitrophenol is detected with a visible spectrophotometric ELISA reader.

Antibodies for an assay of the invention can be produced using lymph node endothelial cell surface sulfated glycoproteins which comprise oligosaccharide biological ligands specifically recognized by LHR for lymph nodes. As described more fully below, two such glycoproteins, $Sgp^{50}$ (i.e., GlyCAM-1) and $Sgp^{90}$, (i.e., CD34) have been identified. Having identified ligand-bearing glycoproteins, one of skill will recognize that a number of modifications of the glycoproteins that do not significantly alter the LHR binding activity are possible. Such modifications include enzymatic or chemical treatment of the proteins to produce fragments that comprise the carbohydrate ligand recognized by LHR. For instance, fragments of the extracellular region of the proteins can be obtained by treatment of the isolated glycoproteins with an appropriate protease such as trypsin, pronase, papain, pepsin and the like.

The extracellular region of the cell surface glycoproteins includes all sequences from the proteins outside the transmembrane and intercellular regions. The extracellular region of the glycoproteins used to generate an antibody comprises a carbohydrate ligand specifically recognized by LHR. The extracellular region may also contain sequences from the transmembrane region (less than about 10 amino acids), so long as solubility is not substantially affected. The term "compound comprising the extracellular region" includes any compound in which the extracellular region, or fragment thereof, is conjugated to a second moiety. The term also embraces the isolated extracellular region and the isolated full length glycoprotein. An "isolated compound comprising the extracellular region" includes such a compound (e.g., a full length glycoprotein) in other than its native state, that is, not associated with an endothelial cell. For instance, the compound may be recombinantly produced, solubilized from the appropriate cell, or associated with a liposome.

Analysis of sulfated glycoproteins of the present invention has revealed that the oligosaccharide moieties recognized by LHR are O-linked. Thus, they can be cleaved from the protein in backbones by beta elimination and borohydride reduction according to standard techniques (see, e.g., Fukuda, *Meth. Enzymol.* 179:17–29 (1989), which is incorporated herein by reference).

The sulfated glycoproteins, or fragments thereof, can be isolated using soluble LHR as described below. The isolated soluble molecules are then used to generate antibodies which are used in assays of the present invention. The glycoproteins can be used as they are isolated or they can be conjugated to a variety of other compounds to confer an enhanced ability to generate antibodies. Alternatively, neoglycoproteins or neoglycolipids can be prepared based on the carbohydrate chains of the glycoproteins using methods well known in the art (see, e.g., Stowell, et al., *Adv. Carb. Chem and Biochem.* 37:225–281 (1980) and Childs, et al., *Biochem. J.*, 262:131–138 (1989), which are incorporated herein by reference).

In the assays of the present invention antibodies are bound to a solid surface. Many methods for immobilizing biomolecules on solid surfaces are known in the art. For instance, the solid surface may be a membrane (e.g., nitrocellulose), a microtiter dish (e.g., PVC or polystyrene) or a bead. The desired component may be covalently bound or noncovalently attached through unspecific bonding. In the case of neoglycoligands and neoglycoproteins, these selectin binding components may be bound to the solid surface without the use of antibodies.

Solid Substrate Surface

A wide variety of organic and inorganic polymers, both natural and synthetic may be employed as the material for the solid surface to which the antibodies are bound. Illustrative polymers include polyethylene, polypropylene, poly (4-methylbutene), polystyrene, polymethacrylate, poly (ethylene terephthalate), rayon, nylon, poly(vinyl butyrate), silicones, polyformaldehyde, cellulose, cellulose acetate, nitrocellulose, etc. Other materials which may be employed, include paper, glasses, ceramics, metals, metalloids, semiconductive materials, cermets or the like. In addition are included substances that form gels, such as proteins, e.g., gelatins, lipopolysaccharides, silicates, agarose and polyacrylamides or polymers which form several aqueous phases, such as dextrans, polyalkylene glycols (alkylene of 2 to 3 carbon atoms) or surfactants e.g., amphophilic compounds, such as phospholipids, long chain (12–24 carbon atoms) alkyl ammonium salts and the like. Where the solid surface is porous, various pore sizes may be employed depending upon the nature of the system.

In preparing the surface, a plurality of different materials may be employed, particularly as laminates, to obtain various properties. For example, protein coatings, such as gelatin can be employed to avoid non-specific binding, simplify covalent conjugation, enhance signal detection or the like.

To obtain covalent bonding between the antibodies and the surface the surface will usually be polyfunctional or be capable of being polyfunctionalized. Functional groups which may be present on the surface and used for linking can include carboxylic acids, hydroxyl groups, mercapto groups and the like. The manner of linking a wide variety of compounds to various surfaces is well known and is amply illustrated in the literature. See for example Chibata, *Immo-* bilized Enzymes, Chibata, Halsted Press, New York, 1978, and Cuatrecasas, J. Biol. Chem. 245:3059 (1970) which are incorporated herein by reference.

In addition to covalent bonding, various methods for noncovalently binding an antibody to a surface can be used. Noncovalent binding is typically nonspecific absorption of an antibody to the surface. Typically, the surface is blocked with a second compound to prevent nonspecific binding. Alternatively, the surface is designed such that it nonspecifically binds one component but does not significantly bind another. For example, a surface bearing a lectin such as Concanavalin A will bind a carbohydrate containing compound but not a labelled protein that lacks glycosylation. Various solid surfaces for use in noncovalent attachment of assay components are reviewed in U.S. Pat. Nos. 4,457,576 and 4,254,082, which are incorporated herein by reference. The surface can be designed to selectively bind antibodies.

Non-radioactive labels may be attached to any molecule which will readily bind the immunoglobulin component of the chimeric molecule. Generally, a ligand molecule (e.g., biotin) is covalently bound to the molecule which binds to the immunoglobulin. The ligand then binds to an anti-ligand (e.g., streptavidin) molecule which is either inherently detectable or covalently bound to a signal system, such as a detectable enzyme, a fluorescent compound, or a chemiluminescent compound. Ligands and anti-ligands may be varied widely. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with antibody.

The molecules which bind to the immunoglobulin can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluoroescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various signal producing systems which may be used, see, U.S. Pat. No. 4,391,904, which is incorporated herein by reference.

EXAMPLES

The following examples are put forth so as to provide those of ordinary skill in the art with a complete disclosure description of how to make the assays, the assay components, and carry out the assays of the invention and are not intended to limit the scope of what is regarded as the invention. Efforts have been made to ensure accuracy with respect to numbers used (e.g., amounts, temperature, etc.) as well as the nomenclature used but some experimental error and deviation should be accounted for. Unless indicated otherwise, parts is parts by weight, molecular weight is weight average molecular weight, temperature is in degree centigrade and pressure is at or near atmospheric.

Example 1

Assay Using L-Selectin

The CAMO2 antibody is diluted to a concentration of 1.6 µg/ml in PBS with 0.1% $NaN_3$, and 100 µl of this solution is dispensed into each well of a 96-well plate. The plate is incubated overnight at 4° C. to allow adsorption of the antibody onto the solid support. The plate is then washed three times with PBS containing 0.1% tween, and blocked with 200 µl/well of a 3% solution of BSA in PBS for 2 hours at room temperature.

A crude GlyCAM-1 preparation is produced by extracting mouse serum with chloroform/methanol solution, followed by dialysis against PBS. After removing the blocking solution, 100 µl of this solution is dispensed into each well, and the plate is incubated for 1 hour at room temperature.

Chimeric molecules of the invention and more specifically, complexes of L-selectin with a secondary antibody and streptavidin-alkaline phosphates are formed as follows:

L-selectin:

2 mg/ml L-selectin-IgG chimera

2/1000 dilution of biotinylated goat anti-human Fc $F(ab')_2$ (Caltag)

2/1000 dilution of streptavidin-alkaline phosphatase (Caltag)

In PBS with 2% BSA and 5% normal rabbit serum

In a separate 96-well plate, 80 µl of serial dilutions of the test inhibitors dissolved in PBS are dispensed into each well. To each inhibitor-containing well is added 80 µl of the selectin-IgG/antibody/streptavidin-alkaline phosphatase complex solution. The plate is then incubated for 30 minutes at 4° C.

The plate containing $CAMO_2$ antibody and captured GlyCAM-1 is washed three times with PBS/0.1% TWEEN detergent, and 100 ml of each selectin complex/inhibitor mixture is transferred to the wells of the GlyCAM-containing plate. This plate is then incubated for 30 minutes at room temperature.

Finally, the solutions are removed from the GlyCAM-1 plate and the plate is washed three times with PBS/0.1% TWEEN detergent. 100 ml of alkaline phosphatase substrate solution (p-nitrophenyl phosphate in ethanolamine/$MgCl_2$) buffer is added to each well to detect the presence of bound selectin complex and the plate is quantified with a 96-well plate reader at 405 nm.

The concentrations required for 50% inhibition ($IC_{50}$) for several synthetic and naturally occurring compounds are shown in Table 1.

Example 2

Assay Using P-Selectin

The CAMO2 antibody is diluted to a concentration of 1.6 µg/ml in PBS with 0.1% $NaN_3$, and 100 µl of this solution is dispensed into each well of a 96-well plate. The plate is incubated overnight at 4° C. to allow adsorption of the antibody onto the solid support. The plate is then washed three times with PBS containing 0.1% tween, and blocked with 200 µl/well of a 3% solution of BSA in PBS for 2 hours at room temperature.

A crude GlyCAM-1 preparation is produced by extracting mouse serum with chloroform/methanol solution, followed by dialysis against PBS. After removing the blocking solution, 100 µl of this solution is dispensed into each well, and the plate is incubated for 1 hour at room temperature.

Chimeric molecules of the invention and more specifically, complexes of P-selection with a secondary antibody and streptavidin-alkaline phosphates are formed as follows:

P-selectin:

4 µg/ml P-selectin-IgG chimera

2/1000 dilution of biotinylated goat anti-human Fc $F(ab')_2$ (Caltag)

2/1000 dilution of streptavidin-alkaline phosphatase (Caltag)

In PBS with 0.2% BSA and 5% normal rabbit serum

Example 3

Assay Using E-Selectin

The CAMO2 antibody is diluted to a concentration of 1.6 μg/ml in PBS with 0.1% NaN$_3$, and 100 μl of this solution is dispensed into each well of a 96-well plate. The plate is incubated overnight at 4° C. to allow adsorption of the antibody onto the solid support. The plate is then washed three times with PBS containing 0.1% tween, and blocked with 200 μl/well of a 3% solution of BSA in PBS for 2 hours at room temperature.

A crude GlyCAM-1 preparation is produced by extracting mouse serum with chloroform/methanol solution, followed by dialysis against PBS. After removing the blocking solution, 100 μl of this solution is dispensed into each well, and the plate is incubated for 1 hour at room temperature.

Chimeric molecules of the invention and more specifically, complexes of E-selection with a secondary antibody and streptavidin-alkaline phosphates are formed as follows:

E-selectin:

4 μg/ml E-selectin-IgG chimera

2/1000 dilution of biotinylated goat anti-human Fc F(ab')$_2$ (Caltag)

2/1000 dilution of streptavidin-alkaline phosphatase (Caltag)

In PBS with 0.2% BSA and 5% normal rabbit serum

Example 4

The three assays as per Examples 1–3 were used to show that serum GlyCAM-1 will bind to each of the different selectins. When Ig chimeras of the three selectins are directly compared for the binding to immobilized serum GlyCAM-1, L-selectin binds at the lowest concentration and binds to higher levels than the other two. (See FIG. 5). However, the signals of the latter two selectins can be made comparable to that of L-selectin by increasing the concentration of the chimera and by lowering the concentration of BSA in the binding step. These specific conditions are described in detail in Examples 1–3.

Example 5

Figure 6:
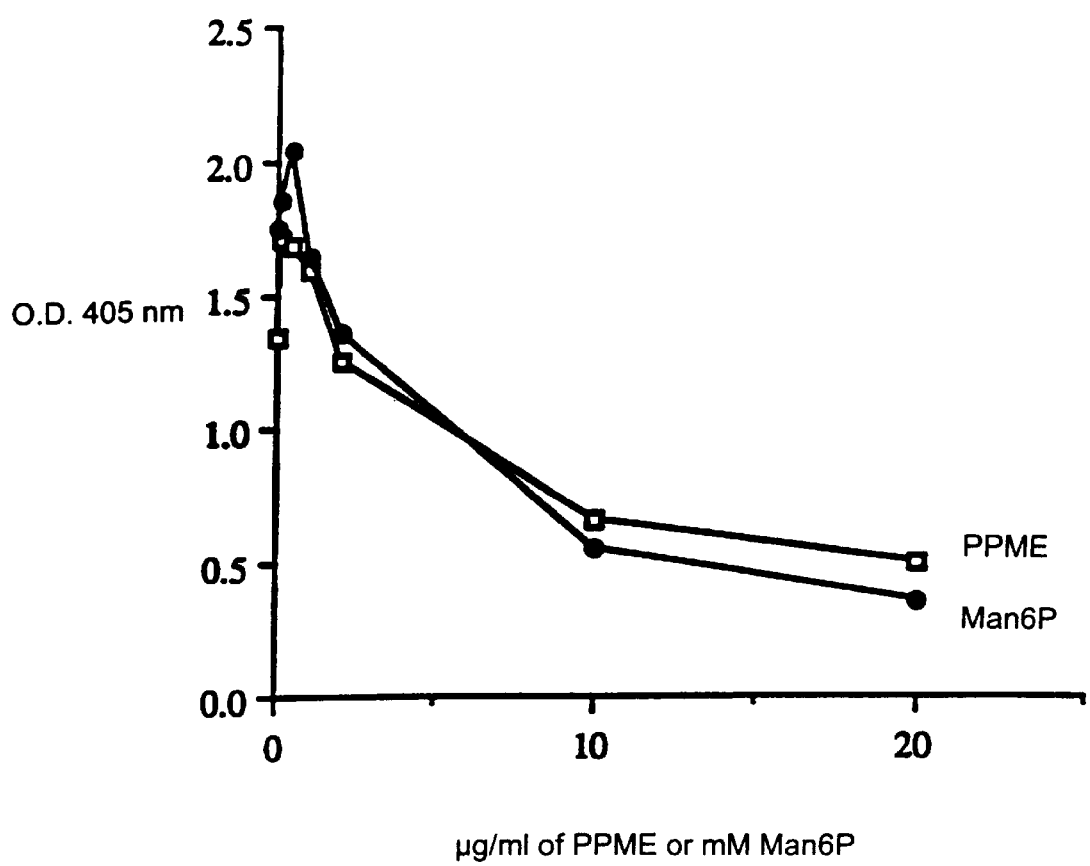
FIG. 6 is a graph showing different compounds tested in an assay of the invention.

The sensitivity of the L-selectin assay of Example 1 was tested and the results are in FIG. 6. Interaction of L-selectin with GlyCAM-1 was inhibited by calcium chelation with EDTA, mannose-6-phosphate, PPME and fucoidin. The assay is at least 10-fold more sensitive than previous assays as measured by IC$_{50}$ determinations with mannose-6-phosphate and fucoidin as test inhibitors.

Example 6

Assays as per Example 1–3 were used to determine IC$_{50}$'s for the inhibition of L-, P- or E-selectin binding to GlyCAM-1 for a number of compounds. The results obtained are shown below in Table 1.

TABLE 1

IC$_{50}$'s for the inhibition of L-, P- or E-selectin binding to GlyCAM-1

| Compound | L-selectin | P-selectin | E-selectin |
| --- | --- | --- | --- |
| mannose-6-phosphate | 1.5 mM | NI* | NI |
| fucoidan | 0.2 μg/ml | 0.02 μg/ml | NI |
| phytic acid | 2 μM | 0.2 μM | NI |
| 3'-sulfo Lewis a | 1.7 mM | 140 μM | 4 mM |
| 3'-sulfo Lewis x | 3 mM | 3 mM | 4 mM |
| 6'-sulfo lactose | 10 mM | | |
| 3',6'-disulfo lactose | 400 μM | | |
| 3',4',6'-trisulfo lactose | 200 μM | | |
| galactose disulfate | 10 mM | | |
| galactose trisulfate | 1.5 mM | | |

*NI indicates no measurable inhibitory activity

The results of Table 1 demonstrate that the assay of the present invention is not only highly sensitive but highly selective.

The instant invention is shown and described herein in what is considered to be the most practical, and preferred embodiments. It is recognized, however, that departures may be made from the specific embodiments described which departures are within the scope of the invention. Further, it is recognized that obvious modifications will occur to one that's skilled in the art upon reading the present disclosure.

What is claimed is:

1. A method for assaying a test compound for its ability to inhibit intercellular adhesion mediated by a selectin, said method comprising:

contacting sgp$^{50}$ immobilized on a solid surface with said test compound and a chimeric molecule comprising of an immunoglobulin component and a selectin component of said selectin under conditions sufficient to allow for specific binding between said chimeric molecule and said sgp$^{50}$;

detecting binding between said chimeric molecule and said sgp$^{50}$; and determining the ability of said test compound to inhibit intercellular adhesion mediated by said selectin from said detection.

2. The method according to claim 1, wherein said selectin is selected from the group consisting of L-selectin, E-selectin and P-selectin.

3. The method according to claim 1, wherein said chimeric molecule further consists of a member of signal producing system.

4. The method according to claim 3, wherein said member is an enzyme capable of converting a substrate to a detectable product and said method further comprises contacting said bound chimeric molecule with said substrate.

5. The method according to claim 4, wherein said enzyme is a phosphatase, esterase, glycosidase or oxidoreductase.

6. A method for assaying a test compound for its ability to inhibit intercellular adhesion mediated by a selectin and sgp$^{50}$, said method comprising:

contacting sgp$^{50}$ immobilized on a solid surface with said test compound and a chimeric molecule comprising an immunoglobulin component a selectin component of said selectin, and a member of a signal producing system under conditions sufficient to allow for specific binding between said chimeric molecule and said sgp$^{50}$;

separating unbound chimeric molecule from said solid support;

detecting chimeric molecule bound to said sgp$^{50}$; and determining the ability of said test compound to inhibit intercellular adhesion mediated by said selectin from said detection.

7. The method according to claim 6, wherein said member of a signal producing system is an enzyme member of signal producing system and said detecting comprises contacting said chimeric molecule with a substrate which is enzymatically converted to a detectable product.

8. The method according to claim 6, wherein said chimeric molecule and said test compound are combined into a reaction mixture and said reaction mixture is then contacted with said substrate.

9. The method according claim 6, wherein said selectin is selected from the group consisting of L-selectin, P-selectin and E-selectin.

* * * * *